United States Patent [19]
Murakami et al.

[11] Patent Number: 5,304,605
[45] Date of Patent: Apr. 19, 1994

[54] BLOOD SEPARATION COMPOSITION

[75] Inventors: Kazunori Murakami, Kusatsu; Tetsuo Takuchi, Yao, both of Japan

[73] Assignees: Nissho Corporation, Osaka; Hokoku Oil Mill Co., Ltd., Yao, both of Japan

[21] Appl. No.: 904,325

[22] Filed: Jun. 25, 1992

[30] Foreign Application Priority Data

Jun. 25, 1991 [JP] Japan .................................. 3-153236

[51] Int. Cl.$^5$ ................................................ C08K 5/20
[52] U.S. Cl. .................................... 524/227; 524/191; 252/60; 252/315.01; 252/315.1; 252/315.2
[58] Field of Search ................... 524/191, 227; 252/60, 252/315.01, 315.1, 315.2

[56] References Cited

U.S. PATENT DOCUMENTS 5,093,019  3/1992  Tagawa et al. ...................... 526/324

FOREIGN PATENT DOCUMENTS 0075119  3/1983  European Pat. Off. .

Primary Examiner—Paul R. Michl
Assistant Examiner—Edward Cain
Attorney, Agent, or Firm—Armstrong, Westerman, Hattori, McLeland & Naughton

[57] ABSTRACT

A blood separation composition for use in blood collection tubes. The composition comprises a fatty acid amide(s) blended with a gel-like material which is the main ingredient of said composition. The amide(s) render(s) stable and less flowable the blood separation composition during storage, allowing it to form a stable partition barrier in each collection tube when centrifuged, with the blood cells above the barrier being prevented from remaining within the serum. The blood separation composition containing the fatty acid amide(s) does not release any harmful oily substance.

7 Claims, No Drawings

BLOOD SEPARATION COMPOSITION

BACKGROUND OF THE INVENTION

1. Field of the Invention

The present invention relates to a blood component-separating composition (hereinafter referred to as "blood separation composition") which is employed in a centrifugal separation method to separate serum or plasma from whole blood, wherein the difference in specific gravity between them is utilized.

2. Prior Art

Many kinds of blood separation compositions which have been proposed are useful in the centrifugal method of blood separation. Those prior art separation compositions contain as their main ingredient a gel-like material such as silicone oil, a chlorinated polybutene, an acrylic polymer or a copolymer of an α-olefin and a diester of maleic acid. Typical additives blended with the main ingredient are a thixotropic agent for enhancing important properties of the gel-like material; and an inorganic substance. The thixotropic agent causes the gel-like material not to flow within the blood collection tubes but to stay on the bottom of the tubes while being transported. When centrifugal force is applied to the collection tubes filled with blood, the gel-like material moves upwards and forms a partition barrier between the serum (or plasma) and the clot. The thixotropic agent also enhances the strength and stability of the partition barrier. On the other hand, an inorganic substance such as titanium dioxide and calcium carbonate is blended with the gel-like material so as to adjust its specific gravity.

The molecules of the thixotropic agents in the prior art blood separation compositions generally have functional groups capable of forming hydrogen bonds. The thixotropic agents are thus either inorganic fine powders such as silica and clay, or organic gelling agents.

There are observed many disadvantages inherent in the prior art thixotropic agents, as summarized below. The inorganic powder such as silica has a specific density which is too high compared with that of the gel-like material used as the main ingredient. If the inorganic powder is blended at a content sufficient to realize a required level of viscosity, then the specific gravity of the blood separation means will often rise above a desirable range of 1.035 to 1.060. On the contrary, adjustment of the specific gravity to fall within this range will be accompanied by an undesirably low viscosity. Thus, it has been difficult to meet the requirement of specific gravity concurrently with the requirement of viscosity. It is another problem that, due to the high specific gravity of the inorganic powder, the actual specific gravity of the blood separation means cannot be kept at a constant level but varies among production lots thereof and over the course of time. In addition, poor compatibility of a rich content of inorganic powder with the gel-like material will cause some fractions of the separation composition to be dispersed in the serum phase (or plasma phase), forming an oily substance which floats therein. Such floating particles are likely to clog the nozzles in an automatic analyzer. Further, because of insufficient strength of the partition barrier, perfect centrifugal isolation of the serum (or plasma) from the clot is not ensured. A number of blood cells will remain in the serum phase above the partition, thus impairing the separation accuracy.

In a case wherein the thixotropic agent added to the blood separation composition is an organic gelling agent, for example, a sorbitol-aromatic aldehyde condensation product, a very low content suffices for a desired level of thixotropy. The extremely low content however brings about inevitably a large variation of viscosity between production lots of said separation composition. The use of such a blood separation composition forms an unstable partition barrier. Moreover, the intermolecular attraction of such an organic gelling agent becomes intensive during the course of time to such a degree as to increase the minimum shear stress for solation of the separation composition. This means poor stability during storage, and the blood separation composition after being stored for a long time will not smoothly rise (or "ascent") within the centrifuged collection tube, thus lowering its separation capability.

SUMMARY OF THE INVENTION

An object of the present invention, therefore, is to provide a blood separation composition free from the aforementioned drawbacks of the prior art separation composition.

The blood separation composition provided in the invention is characterized by (a) fatty acid amide(s) as the thixotropic agent which is added to a gel-like material to enhance the thixotropic property.

THE PREFERRED EMBODIMENTS

The inventors have conducted research to achieve the object and found that (a) fatty acid amide(s) having a low specific gravity can be used as an effective thixotropic agent, which gives an advantage that the blood separation composition can be easily and favorably controlled with respect to not only its specific gravity but also its viscosity at the same time. Unlike the prior art separation composition employing an inorganic powder as a thixotropic agent, fractions of the present separation means do not form an oily substance which floats within the phase of serum (or plasma). Owing to a sufficient strength of the partition barrier formed with the separation composition, no blood cells remain within the serum. In contrast with the conventional organic gelling agent, the molecules of fatty acid amides do not tend to aggregate together during storage and thus do not render it difficult for the separation composition to rise in the centrifuged tubes. The blood separation composition of the invention well maintains its high separating capability for a long time, and is therefore of a higher practical value.

Now, the invention will be summarized below in more detail

The thixotropic agent employed in this invention is any appropriate one of fatty acid amides inert to blood, or any mixture thereof. The number of carbon atoms per one molecule of the amide is from 10 to 25, and more desirably from 16 to 18.

With more than 25 atoms per molecule, the property of the fatty acid amide will be affected adversely by an alkyl group included therein, thus making it difficult to render the blood separation means thixotropic. If however the molecule includes less than 10 atoms, then its melting point will be too low for the amide to be thermally stable, and the separation composition can not be stored in a stable state for a long time.

The preferable content of fatty acid amide in the blood separation means is from 0.5 to 7 parts, or more desirably from 1 to 4 parts by weight per 100 parts by weight of a gel-like material as the main ingredient. In a case wherein less than 0.5 part by weight of the amide is contained, the partition barrier will be weak and apt to be fluidized, thereby disabling the composition to fully perform its separating function. Further, storage stability will also be insufficient because its state is not kept stable during storage. An amide content of more than 7 parts by weight will however render the separation means so flowable that it does not smoothly rise within the centrifuged tubes. Such an excessive quantity of the amide cannot be dispersed uniformly in the gel-like material, also impairing the function of said separation composition.

Any of the unusually used gel-like materials can be selected as the gel-like material in the invention insofar as they preferably have a specific gravity of 1.035–1.055 and a viscosity of 30,000–150,000 cP, at 25 degrees C. With a specific gravity below 1.035 and a viscosity lower than 30,000 cP, the blood separation composition is too mobile to stand still within the tubes when gravitational force or the like is imparted to it during storage. In detail, the separation composition in this case can move close to a rubber stopper which seals an open top of the previously evacuated blood collection tube, even if it is received therein so as to rest on the bottom thereof at first. Consequently, it will not only be mixed with and thus contaminate a centrifugally separated serum or plasma, but also will be left sticking to the rubber stopper, thus making it difficult to obtain a pure sample of serum or plasma. Such a separation composition will rise from the bottom at an accelerated time so that the partition barrier is formed too early to prevent the blood cells from completely sinking below the barrier. Thus, the blood cells remaining within the fraction above the barrier will impair its separating capability.

On the contrary, a specific gravity above 1.055 in combination with a viscosity higher than 150,000 will impair the smooth rising of the separation composition, also failing to enhance a desirable capability of separation. The excessively high viscosity will cause further disadvantages such as difficult handling and allocation of the separation means to a number of collection tubes.

A preferred gel-like material is a copolymer (or more exactly "terpolymer" in this case) of sebacic acid with a mixture of 2,2dimethyl-l,3-propanediol and 1,2-propanediol (as described in our related United States patent application filed on even date herewith). The molar ratio of the mixture to the sebacic acid forming the copolymer is desirably from 1.02 : 1 to 1.07 : 1.

The blood separation composition of the invention can readily be produced for example by conducting the steps of: heating a given amount of the gel-like material to a temperature between 60 degrees C and 80 degrees C; adding thereto an appropriate amount of the fatty acid amide(s); and continuing to stir this mixture with a sufficient shearing stress, while maintaining the temperature, until the amide(s) is completely dissolved in the gel-like material.

The blood separation composition prepared in this manner in the invention need have a specific gravity intermediate those of the serum or plasma and the clot. The separation composition placed in blood collection tubes usually rests on the bottom thereof. Therefore, a larger difference in specific gravity between the separation composition and the clot or blood cells is advantageous in that the centrifuged separation composition can ascent within the tubes more smoothly and more rapidly. On the other hand, a separation composition having an overall specific gravity not exceeding 1.035 includes a fraction whose specific gravity is much lower than 1.035. This fraction may undesirably migrate from said composition into the centrifugally separated serum phase or plasma phase.

Besides the specific gravity as prescribed above, the blood separation composition which is composed of the gel-like material and the predetermined amount of fatty acid amide(s) preferably has a viscosity from to 4,000 cP at 25 degrees C (when measured in the same manner as will be described in the Examples given below).

The specific gravity as well as viscosity of the separation means can be adjusted, if necessary, by further using a conventional thixotropic agent such as silica and/or a conventional gravity-adjusting inorganic substance such as titanium dioxide.

EXAMPLES

The following Examples are given only by way of example, with no intention of delimiting thereto the scope of the present invention.

Viscosities described in the Examples were measured using an "E-Type Viscometer" which is a rotary viscometer (with a cone angle at 3 degrees and a diameter of 28 mm, made by TOKYO KEIKI CO., LTD.). Specific gravities were measured according to the Cupric Sulfate Method using cupric sulfate solutions of different concentrations. One drop of each sample was put in the solutions, in order to find which of them neither caused the drop to rise to the surface nor sink to the bottom. The thus found solution ought to have the same specific gravity as the tested sample.

PREPARATION OF COPOLYMERS

Copolymer No. 1

Copolymers of sebacic acid may be produced by any conventional method known in this field of art.

Polymerization was carried out in a four-mouthed flask comprising a stirrer, a thermometer, an $N_2$ gas-introducing tube and a Vigreaux column. This Vigreaux column of a medium length comprised in turn a distillation head and a condenser which was composed of a thermometer and a receptacle. The condenser was arranged to distill water and/or an amount of excessive diol, under atmospheric or reduced pressure. Reactants which were involved in this process are as follows.

202 grams of sebacic acid, 89 grams of 2,2-dimethyl-1,3-propanediol and 16 grams of 1,2-propanediol were put in the four-mouthed flask to thereby form a reaction mixture. This mixture was heated up to about 225 degrees C, by continuously removing water therefrom while maintaining the vapor temperature almost constant to fall within a range of about 100°–120° degrees C. Upon detection of a reduced rate of water generation after about 4 hours from the start of reaction, a small amount of a titanium compound as an esterification catalyst (at a ratio corresponding to 0.005% of the initial weight of the reactants) was added. At the same time, the reaction system pressure was reduced to 70–100 mmHg, and reaction was continued for 5 hours under this condition. Subsequent to this phase of the process, the pressure was reduced below 5 mmHg for a further reaction for 3 hours. A highly viscous product was discharged from the flask and cooled to room temperature to give a yield of 98%. This product's viscosity was 35,000 cP, and the specific gravity was 1.041 at 25 degrees C. Its molecular weight was 3,800.

Copolymer No. 2

202 grams of sebacic acid, 87 grams of 2,2-dimethyl-1,3-propanediol and 15 grams of 1,2-propanediol were put in the four-mouthed flask to form another reaction mixture. Reaction to produce a copolymer was carried out in the same manner as for the copolymer No. 1, except that the total reaction time was 15 hours including the last phase for 3 hours with a pressure kept at 1.5 mmHg. The yield of copolymer No. 2 obtained in this manner was 95%, its viscosity being 150,000 cP with a specific gravity of 1.041 at 25 degrees C. Its molecular weight was 6,600.

Copolymer No. 3

202 grams of sebacic acid, 88 grams of 2,2-dimethyl-1,3-propanediol and 16 grams of 1,2-propanediol were put in the four-mouthed flask to form still another reaction mixture. Reaction to produce a copolymer was carried out in the same manner as for the copolymer No. 1, except that the total reaction time was 15 hours including the last phase for 3 hours with a pressure kept at 1.5 mmHg. The yield of copolymer No. 3 obtained in this manner was 95%, its viscosity being 68,000 cP with a specific gravity of 1.041 at 25 degrees C. Its molecular weight was 4,400.

PREPARATION OF BLOOD SEPARATION COMPOSITIONS

Example No. 1

This example of the blood separation composition was prepared by blending 2 parts by weight of stearamide (containing a small mixed amount of palmitamide) with 100 parts by weight of the copolymer No. 1. The composition of Example No. 1 showed a viscosity of 140,000 cP and a specific gravity of 1.043 at 25 degrees C.

Example No. 2

3 parts by weight of stearamide were blended with 100 parts by weight of the copolymer No. 1 to give Example No. 2 of a blood separation composition having a viscosity of 187,000 cP and a specific gravity of 1.042 at 25 degrees C.

Example No. 3

2 parts by weight of stearamide were blended with 100 parts by weight of the copolymer No. 2 to give Example No. 3 of a blood separation composition having a viscosity of 260,000 cP and a specific gravity of 1.041 at 25 degrees C

Example No. 4

3 parts by weight of stearamide were blended with 100 parts by weight of the copolymer No. 3 to give Example No. 4 of a blood separation composition having a viscosity of 156,000 cP and a 5 specific gravity of 1.042 at 25 degrees C.

Example No. 5

4 parts by weight of stearamide were blended with 100 parts by weight of the copolymer No. 3 to give Example No. 4 of a blood separation composition having a viscosity of 187,000 cP at a specific gravity of 1.042 at 25 degrees C.

Reference No. 1

0.01 parts by weight of stearamide were blended with 100 parts by weight of the copolymer No. 3 to give a reference example of a blood separation composition having a viscosity of 80,000 cP and a specific gravity of 1.041 at 25 degrees C.

Reference No. 2

10 parts by weight of stearamide were blended with 100 parts by weight of the copolymer No. 2 to give another reference example having a viscosity of 460,000 cP and a specific gravity of 1.044 at 25 degrees C.

Reference No. 3

2 parts by weight of fine silica ("Aerosil 300", a trademark of Nippon Aerosil Co., Ltd.) were blended with 100 parts by weight of the copolymer No. 1 to give still another reference example having a viscosity of 100,000 cP and a specific gravity of 1.053 at 25 degrees C.

COMPARISON OF EXAMPLES WITH REFERENCES

Example Nos. 1–5 as well as Reference Nos. 1–3 were tested for their stability during storage and their capability of dividing blood phases.

(1) STABILITY DURING STORAGE

Blood collection/separation tubes made of glass and those made of polyethylene terephthalate, having an inner diameter of 13.6 mm, were used. A small amount of a blood separation composition of an "Example" or "Reference" weighing 1.5 grams was put into each tube, and after being kept at 25 degrees C for 24 hours the "flow distance" of said composition was measured at different temperatures. The "flow distance" is the distance between an initial position of the blood separation means and a final position thereof which was measured after predetermined hours of storage had passed. The results of this test are given in Table 1.

As will be seen from the data in the table, the blood separation composition of the present invention was more stable even if stored for a long time, and less flowable when transported or handled otherwise, than the blood separation composition represented by the Reference examples.

TABLE 1

| Material of tube Temperature and period of storage | Flow distance (mm) | | | |
|---|---|---|---|---|
| | Glass | | PET (*) | |
| | 40° C. for 336 hr. | 60° C. for 72 hr. | 40° C. for 336 hr. | 60° C. for 72 hr. |
| Examples | | | | |
| No. 1 | 4 | 8 | 3 | 6 |
| No. 2 | 0 | 1 | 0 | 3 |
| No. 3 | 4 | 8 | 3 | 7 |
| No. 4 | 0 | 1 | 0 | 2 |
| No. 5 | 0 | 0 | 0 | 0 |
| References | | | | |
| No. 1 | 10 | 21 | 9 | 19 |
| No. 2 | 0 | 0 | 0 | 0 |
| No. 3 | 6 | 12 | 5 | 9 |

Notes:
"PET" = polyethylene terephthalate

(2) CAPABILITY OF DIVIDING BLOOD PHASES

Similarly, blood collection/separation tubes made of glass and/or polyethylene terephthalate, having an inner diameter of 13.6 mm, were used. A small amount of blood separation composition of an "Example" or "Reference" weighing 1.7 grams was put into each tube, and kept therein at 25 degrees C for 24 hours after storage at 40 degrees C for 336 hours.

9 ml of human whole blood was put into each tube, and after complete coagulation thereof, the tubes were centrifuged at 1,300 G for 10 minutes ("G" being the gravitational acceleration).

Performance or capability of the blood separation composition was evaluated as to the following items, according to the standards given below.

The term "ascendability" used herein indicates the extent to which the blood separation composition can rise in the centrifuged collection tube previously filled with a given amount of human blood. A rating symbol "+++" ('excellent') was allotted to the separation composition which completely rose within the blood collection tube, while another symbol "++" ('good') means a small amount of said composition remained on the tube bottom. A further rating symbol "+" ('poor') represents a significant amount of the blood separation composition which was left on the bottom, whereas still further symbol "+" ('worst') denotes a quite unsatisfactory rising of the separation composition which fully remained on said tube bottom.

Further, the "stability of partition barrier" between the serum and the clot was judged based on the state of said barrier sticking to the tube wall, when 24 hours had passed after the centrifugal separation process. Similarly to the "rising" property, the rating symbols "+++" (excellent), "++" (good), "+" (poor) and "+" (worst) respectively indicate: the perfectly sticking barrier; partially loosened barrier; significantly loosened barrier; and thoroughly loosened barrier.

The "released amount of oily substance" from the separation means was inspected by observation of the serum surface.

"Reddishness" of the serum was checked to determine whether or not any significant number of blood cells had been left in the serum, and also to determine whether or not hemolysis had occurred.

Test results are given in Tables 2 and 3 respectively for the glass tubes and for the polyethylene terephthalate tubes.

TABLE 2

| | Ascend-ability | Stability of partition | Oily substance released | Reddishness of serum |
|---|---|---|---|---|
| Examples | | | | |
| No. 1 | +++ | ++ | Null | No(*) |
| No. 2 | +++ | +++ | Null | No |
| No. 3 | +++ | ++ | Null | No |
| No. 4 | +++ | +++ | Null | No |
| No. 5 | ++ | +++ | Null | No |
| References | | | | |
| No. 1 | +++ | ± | Null | No |
| No. 2 | ± | +++ | Null | No |
| No. 3 | +++ | ± | Present | A little |

Notes:
"No" = no mixing of blood cells in serum
+++ = excellent
++ = good
+ = poor
± = worst

TABLE 3

| | Ascend-ability | Stability of partition | Oily substance released | Reddishness of serum |
|---|---|---|---|---|
| Examples | | | | |
| No. 1 | +++ | +++ | Null | No(*) |
| No. 2 | +++ | +++ | Null | No |
| No. 3 | +++ | +++ | Null | No |
| No. 4 | +++ | +++ | Null | No |
| No. 5 | ++ | +++ | Null | No |
| References | | | | |
| No. 1 | +++ | ± | Null | No |
| No. 2 | ± | +++ | Null | No |
| No. 3 | +++ | ± | Present | A little |

Notes:
"No" = no mixing of blood cells in serum
+++ = excellent
++ = good
+ = poor
± = worst It will be seen from the data of Tables 2 and 3 that in the blood phase-separating operation using the separation composition provided in the invention, not only ascendability but also stability of the partition barrier are excellent and satisfactory. Besides, there is observed neither any amount of oily substance released nor any extent of hemolysis or any number of blood cells remaining in the serum.

It will now be apparent from the foregoing that the blood separation composition provided by the invention is advantageous in its high separating capability and its good stability which are not affected by a long storage period or the like. It does neither move adversely within the collection tubes during transportation thereof, nor change in its minimum shear stress and its rising property in the centrifugal process, thus maintaining its high capability of separating blood phases. Further, the separation composition is inert to blood so that blood is not absorbed nor is hemolysis caused by it. Radiation sterilization using gamma-rays or the like will not give rise to any physical or chemical change of the separation composition. Further, the separation composition will not release any oily substance which will give an undesirable influence to the operation of testing apparatuses.

What is claimed is:

1. In a blood separation composition comprising:
a gel-like material as a main ingredient and a thixotropic agent added to and blended with the gel-like material; the improvement wherein the thixotropic agent is a fatty acid amide or a mixture of fatty acid amides.

2. A blood separation composition as defined in claim 1, wherein each fatty acid amide contains 10-25 carbon atoms per molecule.

3. A blood separation composition as defined in claim 2, wherein each fatty acid amide contains 16-18 carbon atoms per molecule.

4. A blood separation composition as defined in claim 1, 2 or 3, wherein 0.5-7 parts by weight of the fatty acid amide or mixture of fatty acid amides are blended with 100 parts by weight of the gel-like material.

5. A blood separation composition as defined in claim 4, wherein 1-4 parts by weight of the fatty acid amide or mixture of fatty acid amides are blended with 100 parts by weight of the gel-like material.

6. A blood separation composition as defined in claim 1, wherein the gel-like material is a terpolymer of sebacic acid and a mixture of 2,2-dimethyl-1,3-propanediol and 1,2-propanediol.

7. A blood separation composition as defined in claim 6, wherein the molar ratio of the mixture to the sebacic acid is from 1.02:1 to 1.07:1.

* * * * *